United States Patent
Scott et al.

(10) Patent No.: US 7,141,064 B2
(45) Date of Patent: Nov. 28, 2006

(54) COMPRESSED TISSUE FOR HEART VALVE LEAFLETS

(75) Inventors: Michael J. Scott, Lake Forest, CA (US); Rajesh A. Khanna, Tustin, CA (US)

(73) Assignee: Edwards Lifesciences Corporation, Irvine, CA (US)

(*) Notice: Subject to any disclaimer, the term of this patent is extended or adjusted under 35 U.S.C. 154(b) by 472 days.

(21) Appl. No.: 10/141,145

(22) Filed: May 8, 2002

(65) Prior Publication Data

US 2003/0212454 A1    Nov. 13, 2003

(51) Int. Cl.
*A61F 2/24* (2006.01)
(52) U.S. Cl. .................. 623/2.13; 623/918; 600/36
(58) Field of Classification Search ............... 623/1.26, 623/2.12, 2.13, 901, 908, 922; 600/36; 264/316, 264/494, 219, 239, 195, DIG. 42; 156/245; 8/94.11
See application file for complete search history.

(56) References Cited

U.S. PATENT DOCUMENTS

| | | | |
|---|---|---|---|
| 4,056,854 A | 11/1977 | Boretos et al. | |
| 4,800,054 A * | 1/1989 | Roestenberg | 264/86 |
| 4,994,077 A | 2/1991 | Dobben | |
| 5,021,203 A * | 6/1991 | Larsson et al. | 264/40.3 |
| 5,329,846 A | 7/1994 | Bonutti | |
| 5,411,552 A | 5/1995 | Andersen et al. | |
| 5,489,297 A * | 2/1996 | Duran | 623/2.13 |
| 5,545,222 A | 8/1996 | Bonutti | |
| 5,549,666 A * | 8/1996 | Hata et al. | 623/2.13 |
| 5,662,710 A | 9/1997 | Bonutti | |
| 5,713,953 A * | 2/1998 | Vallana et al. | 623/2.15 |
| 5,888,219 A | 3/1999 | Bonutti | |
| 5,925,063 A * | 7/1999 | Khosravi | 606/200 |
| 5,980,570 A | 11/1999 | Simpson | |
| 6,126,686 A * | 10/2000 | Badylak et al. | 623/1.26 |
| 6,132,472 A | 10/2000 | Bonutti | |
| 2001/0008979 A1 | 7/2001 | Bonutti | |
| 2001/0027344 A1 | 10/2001 | Bonutti | |

FOREIGN PATENT DOCUMENTS

| WO | WO 99/33414 A1 | 7/1999 |
|---|---|---|
| WO | WO 00/47139 A1 | 8/2000 |

* cited by examiner

*Primary Examiner*—Brian E. Pellegrino
(74) *Attorney, Agent, or Firm*—David L. Hauser; Guy L. Cumberbatch

(57) ABSTRACT

A process and system for compressing bioprosthetic tissue for use in medical implants. The process involves placing the tissue between two compressive surfaces and applying a force to reduce any nonuniformity of thickness in the tissue, while at the same time reduce the overall thickness. One particularly useful application is the compression of bioprosthetic sheet during the preparation of heart valve leaflets. Bovine pericardium may be compressed to reduce its thickness by about 50%, and then formed into heart valve leaflets. The thinned leaflets have substantially the same absolute strength as those made from uncompressed tissue, and are particular desirable for use in minimally invasive valves which must be compressed into a small profile. The thin tissue enables a reduction in the overall size of the minimally invasive heart valve for delivery. For instance, rolled MIS valves may be reduced in size to as small as 20 mm in diameter. Desirably, a cross-linking step is combined with the compression step to fix the reduced thickness of the tissue. One apparatus may include porous compression substrates through which a cross-linking solution may diffuse so as to perform the fixation and compression simultaneously.

5 Claims, 2 Drawing Sheets

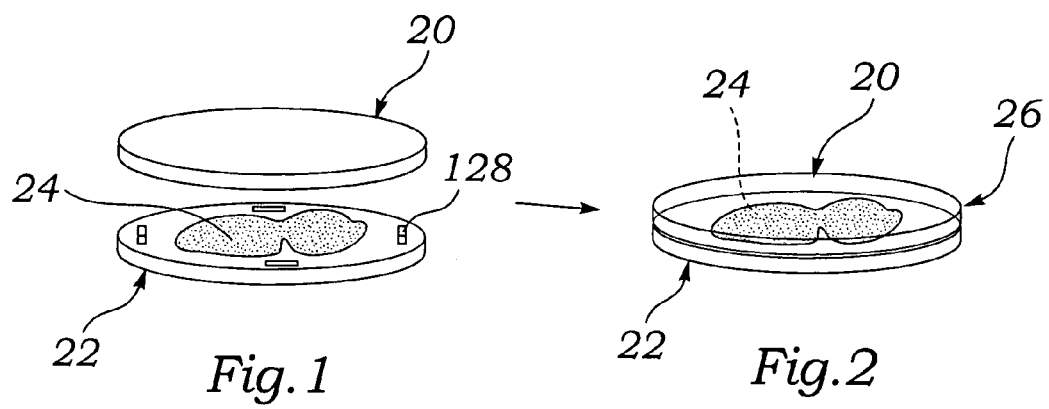
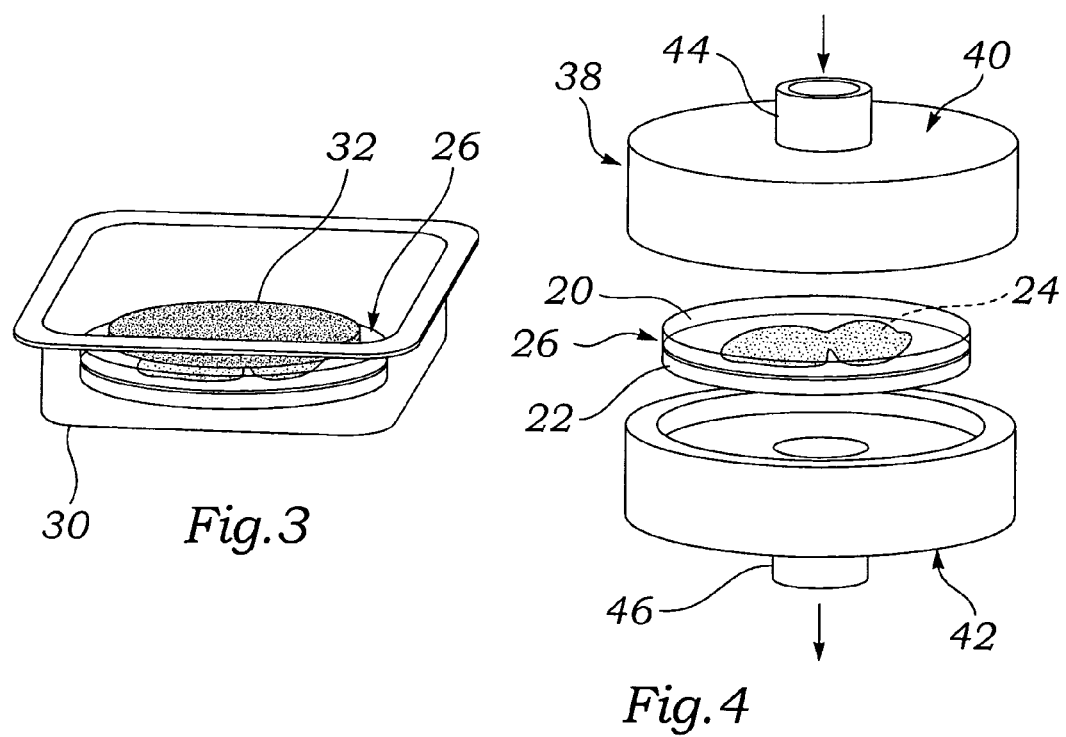

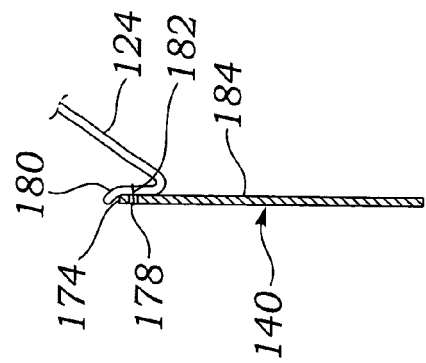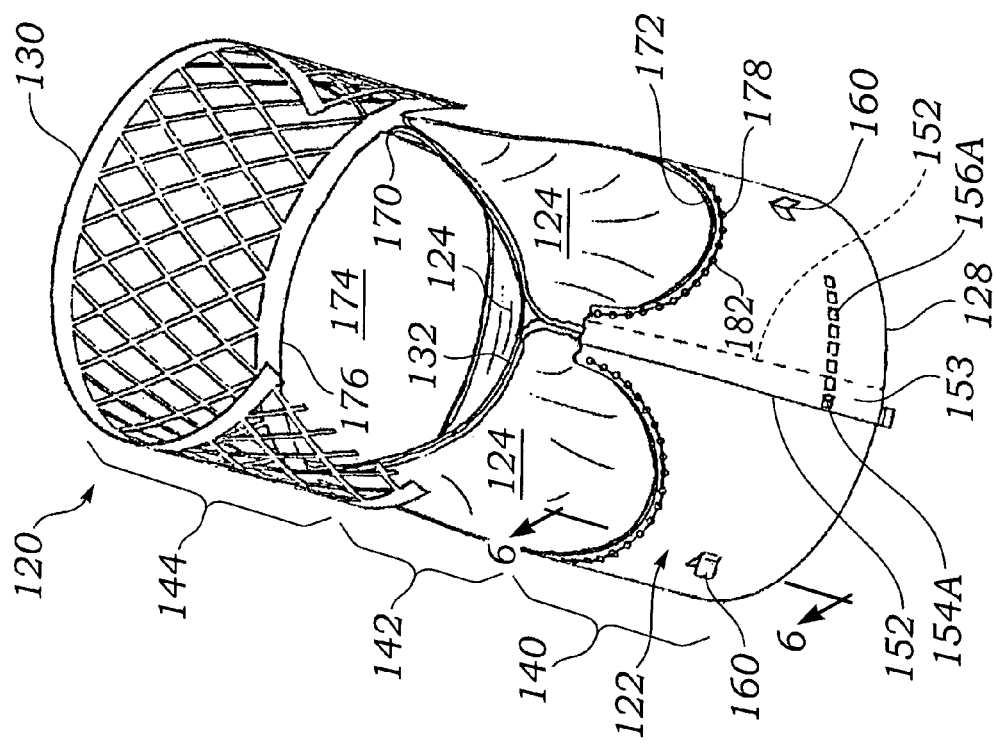

COMPRESSED TISSUE FOR HEART VALVE LEAFLETS

FIELD OF THE INVENTION

The present invention relates generally to medical devices and particularly to compressed bioprosthetic tissue leaflets for heart valve prostheses.

BACKGROUND OF THE INVENTION

Prosthetic heart valves are used to replace damaged or diseased heart valves. In vertebrate animals, the heart is a hollow muscular organ having four pumping chambers: the left and right atria and the left and right ventricles, each provided with its own one-way valve. The natural heart valves are identified as the aortic, mitral (or bicuspid), tricuspid and pulmonary valves. Prosthetic heart valves can be used to replace any of these naturally occurring valves, although repair or replacement of the aortic or mitral valves is most common because they reside in the left side of the heart where pressures are the greatest.

Where replacement of a heart valve is indicated, the dysfunctional valve is typically replaced with either a mechanical valve, or a tissue valve. Tissue valves are often preferred over mechanical valves because they typically do not require long-term treatment with anticoagulants. The most common tissue valves are constructed with whole porcine (pig) valves, or with separate leaflets cut from bovine (cow) pericardium. Also, synthetic materials such as molded polymers have been proposed as substitutes for natural tissue. Although so-called stentless valves comprising a section of porcine aorta along with the valve fully intact are available, the most widely used valves include some form of stent or structural support for the leaflets. Natural tissue valves have a proven track record, but the manufacture thereof suffers from reduced yield of the tissue because of flaws discovered during the inspection process. For example, thickness variations in pericardial tissue renders some pieces unfit for leaflet formation.

A conventional heart valve replacement surgery involves accessing the heart in the patient's thoracic cavity through an incision in the chest. For example, a median sternotomy requires cutting through the sternum and forcing the two opposing halves of the rib cage to be spread apart, allowing access to the thoracic cavity and heart within. The patient is then placed on cardiopulmonary bypass which involves stopping the heart to permit access to the internal chambers. Such open heart surgery is particularly invasive and involves a lengthy and difficult recovery period.

Some attempts have been made to enable less traumatic delivery and implantation of prosthetic heart valves. For instance, U.S. Pat. No. 4,056,854 to Boretos discloses a radially collapsible heart valve secured to a circular spring stent that can be compressed for delivery and expanded for securing in a valve position. Also, U.S. Pat. No. 4,994,077 to Dobbin describes a disk-shaped heart valve that is connected to a radially collapsible stent for minimally invasive implantation.

Recently, a great amount of research has been done to reduce the trauma and risk associated with conventional open heart valve replacement surgery. In particular, the field of minimally invasive surgery (MIS) has exploded since the early to mid-1990s, with devices now being proposed to enable valve replacements without opening the chest cavity. MIS heart valve replacement surgery still typically requires bypass, but the excision of the native valve (in cases where the native valve is removed) and implantation of the prosthetic valve are accomplished via elongated tubes or cannulas. Endoscopes and other such visualization techniques can also be used to assist implantation.

Some examples of more recent MIS heart valves are shown in U.S. Pat. No. 5,411,552 to Anderson, et al., U.S. Pat. No. 5,980,570 to Simpson, U.S. Pat. No. 5,984,959 to Robertson, et al., PCT Publication No. 00/047139 to Garrison, et al., and PCT Publication No. WO 99/334142 to Vesely. Although these and other such devices provide various ways for collapsing, delivering, and then expanding a "heart valve" per se, none of them disclose an optimum structure. For instance, the publication to Vesely shows a tissue leaflet structure of the prior art in FIG. 1, and an expandable inner frame of the invention having stent posts in FIGS. 3A–3C. The leaflets are "mounted to the stent posts 22 in a manner similar to that shown in FIG. 5." Such general disclosures as in Vesely stop short of explaining how to construct a prosthetic valve in a manner that maximizes long-term efficacy. In particular, the means of attaching the leaflets to the MIS stent is critical to ensure the integrity and durability of the valve once implanted.

Another problem with MIS valves of the prior art is their relatively large radial dimension during implantation. Most of these valves utilize one or more radially-expanding stents coupled to a biological valve, and the assembly must be compressed radially and then passed through the lumen of a large bore catheter. Reducing the radial profile of the constricted valve via radial compression is problematic and conflicts with the need for sufficient diameter of the valve in its expanded state to fit securely within an adult heart valve annulus.

Bioprosthetic tissue heart valves have proved particularly successful and durable, and substantially eliminate the need for long-term treatment with anticoagulants. Unfortunately, the use of bioprosthetic tissue in minimally invasive heart valve presents a number of challenges. First, minimally invasive heart valves are most effective if they are compressible into a small profile for delivery and then expandable at the site of implantation. Attachment of the bioprosthetic tissue to the structural component of the valve therefore must be able to withstand the valve compression and expansion. In addition, the xenograft valve or tissue leaflets are likely to be susceptible to damage by folding and pinching during valve compression. The potential for pinching the bioprosthetic tissue is particularly acute when the valve is compressed into a very small profile.

Despite some advances in heart valve design, and particularly MIS valve design, there remains a need for improved tissue characteristics and for a minimally invasive heart valve that can be compressed and expanded without damage to the flexible tissue leaflets.

SUMMARY OF THE INVENTION

The present invention provides improved bioprosthetic tissue leaflets for heart valves having flexible leaflets, including minimally-invasive (MIS) heart valves. After processing in accordance with the present invention, the leaflets have substantially the same tensile strength as leaflets of the prior art, but are significantly thinner, which enables minimally-invasive valves to be reduced to a smaller insertion profile. The process for reducing the leaflet thickness also smooths thickness non-uniformity, which is a benefit for conventional heart valves.

The present invention includes a method of making a heart valve, comprising the steps of providing a sheet material having a first thickness and compressing the sheet material into a modified sheet having a second thickness less than the first thickness but with substantially the same absolute tensile strength as the sheet material. A heart valve leaflet is then formed from the modified sheet.

In a specific embodiment, the sheet material is bioprosthetic tissue, and the method further includes cross-linking the sheet material during or just after the step of compressing. The step of compressing desirably comprises providing two substrates on either side of and in contact with the sheet material and applying pressure to the sheet material with the substrates, and the step of cross-linking comprises contacting the sheet material with a chemical solution. A chemical solution may, but does not necessarily, flow through at least one of the substrates. The substrates may be solid and shims may be provided to limit their spacing and determine the second thickness. The second thickness is desirably less than about 0.23 mm (0.009 in), and in relative terms is desirably less than about 90% of the first thickness, preferably between about 50–60% of the first thickness.

An alternative method of preparing bioprosthetic tissue for implantation includes providing a sheet of bioprosthetic tissue having a first thickness. The sheet of bioprosthetic tissue is compressed into a modified sheet having a second thickness. Finally, the sheet of bioprosthetic tissue is cross-linked during or shortly after the step of compressing. The step of cross-linking is preferably done for a sufficient period of time such that the modified sheet retains its shape. The bioprosthetic tissue may be mammalian pericardium and the step of cross-linking comprises contacting the mammalian pericardium with glutaraldehyde.

The step of compressing may comprise sandwiching the sheet of bioprosthetic tissue between two substrates and applying pressure to the sheet of bioprosthetic tissue with the substrates. The two substrates may be solid or flexible. If the substrates are solid, the spacing between the substrates may be controlled with, for example, shims to determine the second thickness. The step of cross-linking desirably comprises flowing a chemical solution through at least one of the substrates to the tissue. The chemical solution may also be pressurized so as to cause at least one of the substrates to apply pressure to the sheet of bioprosthetic tissue. In one embodiment, the two substrates are semi-permeable and the chemical solution flows through both substrates, either in the same direction or in opposite directions.

The present invention also provides a system for preparing a sheet of material for implantation in a human body. The system includes pair of semi-permeable substrates having cooperating surfaces configured to receive a sheet material therebetween, the cooperating surfaces having similar shapes so that the surfaces sandwich the sheet material therebetween. The system further includes means for compressing the sheet material between the cooperating surfaces to form a modified sheet of reduced thickness, a source of cross-linking solution, and means for contacting the modified sheet with the cross-linking solution. Shims may be provided to limit the spacing of the substrates and thus control the reduced thickness.

In a further embodiment, the present invention provides a heart valve having a structural component, and a plurality of cross-linked bioprosthetic tissue leaflets attached thereto. The leaflets are compressed during cross-linking to reduce their thickness. In one specific embodiment, the bioprosthetic tissue is mammalian (e.g., bovine) pericardium, and the leaflets have a reduced thickness of less than about 0.23 mm (0.009 in). In relative terms, the thickness of the leaflets has desirably been reduced by more than about 10% by compression during fixation. Desirably, the thickness of the leaflets has been reduced to between about 50–60% of its original thickness by compression during fixation.

In an embodiment where the compressed tissue is to be used in an MIS valve, the heart valve structural component may be a tubular stent that has cutouts, the edges to which the leaflets attach. More particularly, the tubular stent is a sheet-like member bent into a tube and having two sides parallel to the tube axis that are joined together. The stent is configured to be delivered in a rolled up spiral with one of the two sides being on the inside of the spiral and the other of the two sides being on the outside of the spiral. Because of the thinner leaflets, the rolled up spiral configuration of the tubular stent desirably has a diameter of less than about 20 mm. Once at the implantation site, the stent can be uncoiled to its expanded state which permits the leaflets to function as a valve.

A further understanding of the nature and advantages of the invention will become apparent by reference to the remaining portions of the specification and drawings.

BRIEF DESCRIPTION OF THE DRAWINGS

FIG. 1 is a perspective view of a separated pair of compression substrates and a tissue sheet placed on an inner surface of one of the substrates;

FIG. 2 is a perspective view of the compression substrates of FIG. 1 brought together to sandwich the tissue sheet therebetween;

FIG. 3 is a perspective view of the compression substrates and tissue sheet sandwich placed in a fluid container and illustrating a dead weight on top of the upper substrate;

FIG. 4 is an exploded perspective view of the compression substrates and tissue sheet sandwich interposed between two halves of a fluid flow chamber;

FIG. 5 is a perspective view of an exemplary expandable heart valve of the present invention incorporating compressed leaflets; and FIG. 6 is a cross-sectional view taken along line 6—6 through one side of the heart valve of FIG. 5 showing a preferred leaflet attachment construction.

DESCRIPTION OF THE PREFERRED EMBODIMENTS

The present invention involves various means for compressing tissue sheet to reduce its thickness for use in medical implants, in particular for use as leaflets in heart valves. It is believed that such tissue sheet compression is novel and has many applications in the medical implant field. For example, the reduced thickness tissue sheet may be used in conventional heart valves, and venous valves, as well as minimally invasive heart valves. One specific example, of a conventional heart valve that may utilize tissue in accordance with the present invention is the Carpentier-Edwards® PERIMOUNT® Pericardial Bioprosthesis, available from Edwards Lifesciences of Irvine, Calif. The basic construction of the PERIMOUNT® valve is seen in U.S. Pat. No. 4,501,030, which disclosure is expressly incorporated herein by reference. An example of a minimally-invasive valve that may utilize tissue in accordance with the present invention is found in U.S. Pat. No. 6,733,525, issued May 11, 2004, entitled "ROLLED MINIMALLY INVASIVE HEART VALVES AND METHODS OF USE," which disclosure is expressly incorporated herein by reference. Furthermore, the modified tissue sheet of the present invention is believed to have superior strength relative to prior tissue sheets having the same thickness, and may prove desirable for such applications as skin grafts and tissue patches. In short, the applications for the modified tissue sheet constructed with the means and methods described herein cannot be limited to the primary application of minimally invasive heart valves.

An application of the present invention is the formation of compressed leaflets for expandable heart valves. In one such application, the leaflets of the present invention are desirably incorporated in expandable prosthetic heart valves that initially roll into a tight spiral to be passed through a catheter or other delivery system and then unfurl or unroll at the implantation site, typically a valve annulus. The heart valves comprise structural stent bodies with a plurality of leaflets incorporated therein. Various materials are suitable for the stent body, although certain nickel-titanium alloys are preferred for their super-elasticity and biocompatibility. It should also be noted that specific stent body configurations disclosed herein are not to be considered limiting, and various construction details may be modified within the scope of the invention.

Various bioprosthetic tissues may be used in the present invention, though a preferred tissue for use in the primary application of heart valve leaflets is bovine pericardial tissue. Though the thickness and strength of bovine pericardial tissue is considered desirable for longer lasting valves, other bioprosthetic tissue such as porcine, equine and other mammalian pericardium may be used. In general, the compression process reduces the thickness of the particular material, without a proportional reduction in its absolute strength. For example, a bovine pericardial sheet having a thickness of 0.40 mm (0.016 inches) may be compressed and reduced in thickness by about 50%, without an accompanying reduction in overall absolute tissue strength. Any tissue sheet that behaves in a like manner is a candidate for the processes of the present invention, though those of skill in the art will appreciate that certain materials may be better suited for any one specific application. Even materials other than bioprosthetic tissue may be modified in accordance with the teachings of the present invention to form compressed material for use in implants. For instance, tissue constructs with a synthetic matrix and tissue ingrowth may be improved through the processes disclosed herein.

One embodiment of the invention involves cross-linking or "fixing" the bioprosthetic tissue during or just after the process of compressing its thickness. Cross-linking the collagenous matrix provides stability prior to implantation to retard degeneration. Further, the fixation process generally operates by blocking reactive molecules on the surface of and within the donor tissue, thereby rendering it substantially non-antigenic and suitable for implantation. Fixing bioprosthetic tissue typically involves contacting the tissue with a cross-linking agent, normally a solution. Exemplary fixing solutions for bioprosthetic tissue such as bovine pericardium include glutaraldehyde, formaldehyde, polyethylene glycol, etc. Other ways to fix tissue exist, including heating, irradiating, etc. The fixing step helps maintain the compressed sheet in its modified form with a reduced thickness. Furthermore, when the compression and cross-linking are done simultaneously the cross-linking fixes the gross shape of the tissue in the form of the compressing surfaces. For example, bovine pericardium tends to be somewhat uneven and curls at its edges, and compression between flat surfaces in conjunction with cross-linking flattens the tissue to facilitate subsequent handling and formation of heart valve leaflets. Of course, the sheet may be compressed and fixed into a particular three-dimensional form for other uses that require such a contour.

In some cases the procedure of compression first and then fixation, rather than performing these steps simultaneously, may be advantageous and achieve the desired reduction in thickness. The fixation may occur relatively quickly and tend to resist the compression forces, thus hindering the process. On the other hand, if the tissue is compressed in its natural state, it may compress further, and then it can be cross-linked after the compression to fix the thickness. The particular sequence desired depends on the material involved, the time for cross-linking, the ultimate use, and other factors.

FIGS. 1–4 illustrate exemplary systems for processing bioprosthetic tissue in accordance with the present invention.

FIG. 1 illustrates a disk-shaped upper substrate 20 separated above a disk-shaped lower substrate 22 on whose upper surface is located a tissue sheet 24. The upper substrate 20 lowers to sandwich the tissue sheet 24 between it and the lower substrate 22, as seen assembled at 26 in the view of FIG. 2. That is, the tissue sheet 24 is sandwiched between the lower surface of the upper substrate 20 and the upper surface of the lower substrate 22. This assembled sandwich 26 of the substrates 20, 22 and tissue sheet 24 is the basic component of the tissue compression process of the present invention. More than one such sandwich 26 may be stacked together to increase yield. In one arrangement, at least two tissue sheets 24 are alternated between at least three substrates 20, 22.

Optionally, shims 28 (four of which are shown for example) may be interposed between the inner surfaces of the substrates 20, 22 to limit their spacing and at the same time limit the thickness to which the tissue sheet 24 is reduced. Alternatively, the magnitude and duration of compression imparted on the tissue sheet 24 to result in a desired thickness can be empirically determined. The substrates 20, 22 are illustrated as being relatively thick, but represent a variety of substrates including relatively thin ones. Likewise, the relative sizes and shapes of the substrates 20, 22 are exemplary only.

The assembled sandwich 26 is seen in FIG. 3 located within a container 30 and having a compressive weight 32 placed thereover. The compressive weight 32 adds to the existing weight of the upper substrate 20 to compress the tissue sheet 24 between the substrates 20, 22. The magnitude of the weight 32 and duration of compression vary depending on the tissue parameters and subsequent application. In one exemplary embodiment, the tissue is bovine pericardium having a maximum dimension across its face of about 6 in. and the weight 32 is about 250 pounds. The weight 32 remains in place for approximately 30 minutes so as to compress and reduce the thickness of the tissue to between about 50–60% of its original thickness. It will be understood that other mechanical means, such as a hydraulic piston, for applying pressure to the upper substrate 20, may be utilized.

In a preferred embodiment, a fluid fills the container 30 to above the level of the upper substrate 20. The fluid may be a cross-linking solution such as glutaraldehyde, or may be a relatively inert solution such as saline. In either case, the substrates 20, 22 are desirably porous to permit the fluid to seep therethrough and contact the compressed tissue sheet 24. For example, the substrates 20, 22 may be made of a porous polymer having a pore size of between about 15–45 microns. Alternatively, the substrate 20, 22 may be made of a porous ceramic. Whatever the material, the substrates 20, 22 are desirably pre-saturated with the fluid to ensure contact of the fluid with the tissue sheet 24 throughout the compression process.

If the fluid is inert, the tissue sheet 24 does not undergo chemical change, but instead just compresses to a reduced thickness. However, immediately after the compression process the tissue sheet 24 is desirably subjected to a cross-linking step to fix or otherwise maintain the reduced thickness. Studies indicate that cross-linking of tissue substantially fixes the overall shape of the tissue. Therefore, if the tissue sheet 24 is compressed flat and then fixed, it typically remains flat. Moreover, cross-linking fixes the reduced thickness and substantially prevents a reversion back to the original thickness.

It should be noted that in most cases the thickness reduction of bioprosthetic tissue by compression is due primarily to fluid, mainly water, being squeezed from the tissue. Thus, if the tissue is fixed during or immediately after the compression, it will retain its reduced thickness even if re-introduced into an aqueous solution. That is, the tissue will not significantly rehydrate because it has been cross-linked and is no longer as porous as the fresh tissue. For example, bovine pericardium tissue may be formed into heart valve leaflets and then assembled into a complete heart valve. The heart valve is typically stored, sometimes for years, in an aqueous solution of glutaraldehyde before implantation during which the compressed tissue of the present invention will substantially retain its reduced thickness. This is beneficial if the leaflets are used in the minimally invasive valves because the reduced thickness enables formation on the relatively low profile of the valve as it is being inserted.

FIG. 4 illustrates an alternative system 38 for compressing the tissue sheet 24 using fluid rather than mechanical compression means. The aforementioned sandwich 26 of the substrates 20, 22 and tissue sheet 24 is shown exploded between an upper housing portion 40 and a lower housing portion 42. Both the upper and lower housing portions 40, 42 define facing cavities such that when the two portions are brought together a hollow chamber therein is created within which the sandwich 26 fits. In addition, the upper housing portion 40 has a fluid inlet 44 and the lower housing portion 42 has a fluid outlet 46. Flow arrows indicate the direction that fluid passes through the assembled system 38.

In operation of the system 38, the upper and lower portions 40, 42 come together in sealing engagement with the sandwich 26 positioned within the hollow chamber. Fluid introduced through the inlet 44 pressurizes the hollow chamber above the sandwich 26 which creates a pressure gradient from top to bottom within the chamber. The substrates 20, 22 are porous such that fluid passes through the upper substrate 20 into contact with the tissue sheet 24, and then passes through the tissue sheet in the same direction through the lower substrate 22 and out the outlet 46. If the fluid is a fixative, the tissue is cross-linked during compression and forcing the fluid through the tissue speeds the process. Not only does the pressure gradient cause the flow of fluid through the sandwich 26, but it also compresses the upper substrate 20 against the lower substrate 22, which compresses the tissue sheet 24 therebetween.

Various arrangements utilizing fluid pressure are contemplated other than the system 38 shown in FIG. 4. For example, only one of the substrates 20, 22 may be porous, with the other one being impermeable to passage of the particular fluid used. In addition, the fluid may not flow through the system 38, but rather static fluid pressure may be applied by flowing fluid in through the outlet 46. In that case, the fluid from both directions may be forced through the porous substrates 20, 22 and then radially outward therebetween.

Furthermore, in addition to rigid substrates 20, 22, the fluid pressure system 38 may utilize flexible substrates. For example, flexible porous polymers or other tissue can be used to sandwich the tissue sheet 24 therebetween, with fluid pressure supplied around the outside to compress the tissue sheet. Of course, positive fluid pressure can be supplied on one side of the compression sandwich, as in the system 38, or a negative pressure can be applied to one side to achieve a pressure gradient.

In an alternative embodiment, a combination of rigid and flexible substrates may be used. Outer rigid substrates having holes therethrough for fluid flow may surround a sandwich of two flexible substrates and the tissue sheet. The flexible substrates, being porous, regulate the rate of fluid flow through the system. One example of such a flexible substrate is a paper-type of filter.

Although the present invention has been described as the most suitable for producing bioprosthetic tissue of reduced thickness, the process and systems shown herein also provide an additional important benefit in that the compression process desirably renders the bioprosthetic tissue more uniform in its thickness. Typical bovine pericardium, for example, has great variation in thickness across even small sheets. Therefore, the unmodified thicknesses mentioned herein are averaged across the sheet. Compression of the tissue in accordance with the present invention greatly reduces thickness non-uniformity. This phenomenon does not require much thickness reduction of the tissue sheet, and reductions as low as 10% may be enough in certain situations to render the tissue uniform in thickness. Therefore, the present invention may also be used to render bioprosthetic tissue more uniform in thickness without substantially reducing its thickness. For example, bovine pericardium having an average thickness of between about 0.30–0.46 mm (0.012–0.018 in.) may be compressed according to the present invention by about 10% to render the thickness substantially uniform. By "substantially uniform," the bovine tissue sheet has a thickness that does not vary by more than about 0.11–0.13 mm (0.004–0.005 inch), as opposed to uncompressed bovine tissue that varies by about 0.22–0.25 mm (0.008–0.01 inch). Thus, the thickness variation is reduced by about 50%.

It should be also noted that the compression surfaces of the substrates are desirably very smooth to render the compressed tissue smooth. If polymer or ceramic substrates are utilized, their compressive surfaces are desirably polished smooth.

The various methods for compressing tissue sheet produce a modified sheet that can then be used in medical implant applications, most notably as heart valve leaflets. The modified sheet is desirably thinner yet just as strong as the unmodified precursor sheet. An exemplary fabrication process involves treating the modified sheet to render it generally inert and safe for human implantation. The treatment typically includes immersing the sheet in a chemical solution such as glutaraldehyde for a predefined period of time to rid the tissue of microbial entities, or "bugs." An exemplary quarantine period is about 14 days. Subsequently, heart valve leaflets are cut from the modified sheet and assembled with other components into a heart valve. The assembly may include three leaflets each with a rounded cusp edge sewn to the outside of the valve and a free edge that extends into the flow path. The three adjacent pairs of free edges meet in the middle of the valve at coapting lines oriented 120° with respect to one another. In the minimally invasive valve described above, the leaflets or membranes attach over apertures arranged around a tubular stent and the free edges billow inward to meet along the coapting lines. The assembled valve is then stored in a sterile fluid, typically glutaraldehyde, for a period prior to implantation.

Again, the improved tissue of the present invention may be used in various types of heart valves, such as the Carpentier-Edwards® PERIMOUNT® Pericardial Bioprosthesis mentioned above. Thin tissue sheets are particularly useful in minimally-invasive valves, such as those disclosed in U.S. Pat. No. 6,533,525.

With reference to FIGS. 5 and 6, an exemplary one-piece prosthetic heart valve 120 is shown that utilizes a tissue sheet prepared in accordance with the present invention. The valve 120 comprises a stent body 122 and a plurality of leaflet-forming membranes 124. The stent body 122 is shown in FIG. 5 in its expanded configuration generally defining a tube centered about an axis. A frontal portion of the stent 122 is cut away in the drawing in order to view the membranes 124. The membranes 124 fasten within the stent body 122 so as to form a one-way valve therewithin, and orient the valve to have an inflow end 128 and an outflow end 130. In a preferred embodiment, there are three such membranes 124 each having a free edge 132 that extends inward from the stent body 122 and coapts or meets the other two free edges generally along radial lines spaced apart 120° with respect to each other to shut the valve during the back flow cycle of blood flow. When blood flows in the opposite direction, from the inflow end 128 to the outflow end 130, the free edges 132 of the membranes 124 move radially outward away from each other to open the valve.

With specific reference to FIG. 5, the tubular stent body 122 comprises three sections, starting at the inflow end 128 and moving toward the outflow end 130: an annulus anchoring section 140, a sinus section 142, and an outflow section 144. The three sections 140, 142, and 144 are desirably formed from a single sheet-like piece of material that can be cohesively rolled into a tight spiral and expanded into the tubular configuration shown. In this regard, the stent body 122 includes an axially-oriented first side edge 150 that mates with an axially-oriented second side edge 152 along a longitudinal seam 153. The two side edges 150, 152 abut or overlap and lock together using one or more, but preferably two or more cooperating tabs 154a and slots 156a.

The heart valve 120 may be implanted using several minimally-invasive approaches, and in one or more stages. For example, the heart valve 120 may be delivered using a pusher, or along with a balloon catheter, through a large bore cannula or catheter (i.e., tube). In one embodiment, the stent, having the flexible membranes thereon, may be stored in an unfurled configuration to reduce stress upon and damage to the membranes, and rolled into a compact tube just prior to use.

In a preferred implantation technique, the prosthetic heart valve 120 expands outward and compresses against the native leaflets which present a relatively uneven base. Even if the leaflets are excised, the circularity of the annulus depends on the skill of the surgeon. Minimizing any openings in the anchoring section 140 enhances its rigidity so as to ensure a relatively tubular support structure for the leaflet-forming membranes 124. However, anchoring barbs 160 may be provided in the anchoring section 140, and may be formed by integrally cut tabs as shown. In addition, openings may be provided in the side wall of the tubular stent body 122 to reduce the roll-up stiffness.

With reference to FIG. 5, the sinus section 142 comprises a plurality (preferably three) of generally axially extending commissures 170 and curvilinear cusps 172 defined by relatively large sinus apertures 174 in the stent body 122. In the illustrated embodiment, the sinus apertures 174 are generally semi-circular with a straight, circumferential edge 176 defined by the beginning of the outflow section 144. As seen also in cross-section in FIG. 6, a plurality of small attachment apertures 178 track along the edge of the sinus apertures 174, extending around the curvilinear cusps 172 and substantially up the entire commissures 170. Fasteners such as sutures 182 secure an outer edge portion 180 of the membranes 124 to the stent body 122 using the attachment apertures 178. The sutures typically loop through the membrane 124 twice at each attachment aperture 178 in a single mattress stitch, though various other stitching techniques are known.

The stent body 122 with attached membranes 124 rolls up for delivery with the first side edge 150 to the inside of the spiral and the second side edge 152 to the outside. To reduce the size of the delivery passage through which the minimally invasive valve passes, the outer diameter of the rolled up valve is desirably as small as possible. One way to reduce the outer diameter of the valve is to reduce the thickness of the stent body 122 and attached membranes 124. The stent body 122 desirably is made of a highly elastic material which can be extremely thin without risk of deformation in the rolled up configuration of the valve. The membranes 124 are desirably constructed of bioprosthetic tissue that has been compressed in accordance with the present invention to reduce its thickness. As mentioned above, a preferred bioprosthetic tissue is bovine pericardium that has been reduced in thickness to about 50–60% of its starting thickness.

Depending on the size of the valve, and the intended use, bovine pericardium having an unmodified thickness of between about 0.30–0.46 mm (0.012–0.018 in.) is desirable. For use in the rolled-type of minimally invasive valves, the thickness of the bovine pericardium may be reduced down to about 10%–90% of its original thickness (or, stated another way, a reduction of 10%–90%). Desirably the thickness of the bovine pericardium may be reduced down to about 50%–60% of its original thickness, and preferably to about 50% of its original thickness. For example, the modified bovine pericardium tissue mentioned above has a thickness of between about 0.15–0.23 mm (0.006–0.009 in.). The reduction in thickness may be accomplished by leaving the tissue sheet compressed for a predetermined period of time, or precision shims may be introduced in between the compressing surfaces to limit their displacement toward one another.

While the foregoing describes the preferred embodiments of the invention, various alternatives, modifications, and equivalents may be used. Moreover, it will be obvious that certain other modifications may be practiced within the scope of the appended claims.

What is claimed is:

1. A method of manufacturing an improved leaflet for a minimally invasive heart valve, comprising:
   providing a substantially flat sheet formed entirely of pericardial tissue and having a starting thickness, the sheet having opposite first and second surfaces;
   placing the sheet of pericardial tissue on a first substrate such that the first surface of the pericardial tissue contacts the first substrate;
   displacing a second substrate such that it contacts the second surface of the pericardial tissue;

applying a compressive force to the sheet of pericardial tissue to reduce the thickness of the pericardial tissue by at least about 10% to a reduced thickness without substantially reducing an absolute tensile strength of the pericardial tissue; and cutting at least one heart valve leaflet from the compressed sheet of pericardial tissue, the reduced thickness leaflet being configured for use with a minimally invasive heart valve.

2. The method of claim 1, wherein the step of applying comprises:

applying a compressive force of at least about 250 pounds for a period of at least about 30 minute.

3. The method of claim 1, wherein the starting thickness is between about 0.30–0.46 mm, and wherein the resulting thickness is less than about 0.23 mm.

4. The method of claim 3, wherein the step of applying a compressive force to the sheet of pericardial tissue reduces its starting thickness by between 50–60%.

5. The method of claim 1, further including placing at least one shim between the first and second substrates to limit the reduction in thickness of the sheet of pericardial tissue.

* * * * *